United States Patent
Greenhalgh et al.

(10) Patent No.: US 9,205,240 B2
(45) Date of Patent: Dec. 8, 2015

(54) POWDER DELIVERY DEVICE

(75) Inventors: Paul Greenhalgh, Buckinghamshire (GB); Joseph Maria Grimbergen, Leiden (NL); Oliver Harvey, Cambridgeshire (GB)

(73) Assignee: PROFIBRIX B.V., Leiden (NL)

( * ) Notice: Subject to any disclaimer, the term of this patent is extended or adjusted under 35 U.S.C. 154(b) by 0 days.

(21) Appl. No.: 13/139,781

(22) PCT Filed: Dec. 15, 2009

(86) PCT No.: PCT/GB2009/051714
§ 371 (c)(1),
(2), (4) Date: Jun. 15, 2011

(87) PCT Pub. No.: WO2010/070333
PCT Pub. Date: Jun. 24, 2010

(65) Prior Publication Data
US 2011/0251580 A1 Oct. 13, 2011

(30) Foreign Application Priority Data

Dec. 15, 2008 (GB) .................................... 0822759.7
Dec. 15, 2008 (GB) .................................... 0822770.4

(51) Int. Cl.
*A61M 35/00* (2006.01)
*A61M 11/00* (2006.01)
*A61M 15/00* (2006.01)

(52) U.S. Cl.
CPC ............... *A61M 35/00* (2013.01); *A61M 11/00* (2013.01); *A61M 11/008* (2014.02);
(Continued)

(58) Field of Classification Search
CPC .................... A61M 2202/064; A61M 15/0086; A61M 2206/16; A61M 15/0091; A61M 35/00; A61M 11/008; A61M 15/0008; A61M 11/00; A61M 35/003; A61M 2202/0425; A61M 2202/0449; A61M 2205/8225

USPC ............................................. 604/24, 58, 500
See application file for complete search history.

(56) References Cited

U.S. PATENT DOCUMENTS 1,929,154 A 10/1933 Sundock
2,151,418 A 3/1939 Bolte
(Continued)

FOREIGN PATENT DOCUMENTS

CN 201216785 Y 4/2009
EP 1477119 A1 11/2004
(Continued)

OTHER PUBLICATIONS

International Preliminary Report on Patentability (Form PCT/IB/373) and Written Opinion of the International Searching Authority (Form PCT/ISA/237) issued Jun. 21, 2011 for the corresponding International Application No. PCT/GB2009/051714.
(Continued)

*Primary Examiner* — Emily Schmidt
*Assistant Examiner* — Lauren M Peng
(74) *Attorney, Agent, or Firm* — Young Basile

(57) ABSTRACT

A device for the topical dispensing of a powder, typically a powder medicament, comprises, or is adapted to be coupled to, a powder receptacle and a gasflow generator. The gasflow generator is adapted, in use, to cause gas to flow through the device, which further comprises an agitator by which the powder and/or the powder receptacle can be mechanically agitated. Actuation of the gasflow generator, which causes gas to flow through the device and to entrain powder from the powder receptacle, thereby to dispense powder from the device, is accompanied by actuation of the agitator, causing the powder receptacle to be mechanically agitated, thereby facilitating the release of powder from the powder receptacle.

19 Claims, 12 Drawing Sheets

(52) U.S. Cl.
CPC ........ *A61M 15/0008* (2014.02); *A61M 35/003* (2013.01); *A61M 2202/0425* (2013.01); *A61M 2202/0449* (2013.01); *A61M 2205/8225* (2013.01)

(56) References Cited

U.S. PATENT DOCUMENTS

| | | | |
|---|---|---|---|
| 2,501,279 | A | 3/1950 | Kark |
| 4,620,847 | A | 11/1986 | Shishov et al. |
| 5,366,122 | A * | 11/1994 | Guentert et al. ............. 222/401 |
| 5,884,621 | A | 3/1999 | Matsugi et al. |
| 6,182,712 | B1 * | 2/2001 | Stout et al. ...................... 141/18 |
| 6,261,258 | B1 * | 7/2001 | Saines ............................. 604/58 |
| 6,971,384 | B2 * | 12/2005 | Gieschen et al. . A61M 15/0086 128/203.12 |
| 7,025,056 | B2 * | 4/2006 | Eason et al. ............. 128/203.15 |
| 2005/0205087 | A1 | 9/2005 | Kablik et al. |
| 2007/0160543 | A1 | 7/2007 | Moller |

FOREIGN PATENT DOCUMENTS

| | | |
|---|---|---|
| EP | 1607117 A1 | 12/2005 |
| FR | 2863503 A1 | 6/2005 |
| GB | 472355 | 9/1937 |
| GB | 539351 | 9/1941 |
| GB | 572015 | 9/1945 |
| GB | 572112 | 9/1945 |
| GB | 607237 | 8/1948 |
| GB | 628675 | 9/1949 |
| GB | 649506 | 1/1951 |
| GB | 668341 | 3/1952 |
| GB | 808273 | 2/1959 |
| GB | 878106 | 9/1961 |
| WO | 9209322 A1 | 6/1992 |
| WO | 9503846 A1 | 2/1995 |
| WO | 2006044800 A2 | 4/2006 |
| WO | 2008106616 A2 | 9/2008 |

OTHER PUBLICATIONS

Cannon et al., Rate of Epithelial Regeneration, Annals of Surgery, Jan. 1943, pp. 85-92.

Klemm, Enhanced Healing of Skin Wounds in Dogs with Systemically and Locally Administered Drugs, Specialia, 1967, pp. 55-57.

* cited by examiner

POWDER DELIVERY DEVICE

CROSS REFERENCE TO RELATED APPLICATIONS

This application claims priority from United Kingdom patent serial numbers UK 0822759.7 filed Dec. 15, 2008 and UK 0822770.4 filed Dec. 15, 2008, both of which are incorporated herein by reference in their entirety.

TECHNICAL FIELD

This invention relates to a device for the dispensing of a powder. The device is of particular utility in surgical procedures or other medical applications, for the topical delivery of a powder to an internal or external surface of the body.

BACKGROUND

Devices for the dispensing of powder onto a surface of the body, or for other purposes, are well known. Examples of such devices are disclosed in the following published documents: GB-A-472,355; GB-A-539,351; GB-A-572,015; GB-A-572,112; GB-A-607,237; GB-A-628,675; GB-A-649,506; GB-A-668,341; GB-A-808,273; GB-A-878,106; U.S. Pat. No. 1,929,154; U.S. Pat. No. 2,151,418; U.S. Pat. No. 2,501,279; U.S. Pat. No. 5,884,621; US-A-2005/0205087; FR-A-2 863 503.

There is an ongoing need for a device that can be used to deliver a powder to a surface of the body, whether an external surface or an internal surface, e.g. a surface exposed during a surgical procedure, in a controlled fashion. It may be necessary or desirable for the powder to be delivered to a highly localized site, i.e. with precision, and/or in a highly uniform manner. There is also an ongoing need for a powder delivery device that achieves these objectives, yet is simple and inexpensive to manufacture and to use.

SUMMARY

There has now been devised an improved form of powder delivery device that addresses these needs and/or overcomes or substantially mitigates disadvantages associated with the prior art.

Thus, according to a first aspect of the invention, there is provided a device for the dispensing of a powder, the device comprising, or being adapted to be coupled to, a powder receptacle and a gasflow generator adapted, in use, to cause gas to flow through the device, and the device further comprising an agitator by which the powder and/or the powder receptacle can be mechanically agitated, the gasflow generator and the agitator being operably linked such that actuation of the gasflow generator, which causes gas to flow through the device and to entrain powder from the powder receptacle, thereby to dispense powder from the device, is accompanied by actuation of the agitator, causing the powder receptacle to be mechanically agitated, thereby facilitating the release of powder from the powder receptacle.

In the device according to the invention, actuation of the gasflow generator, which results in dispensing of powder from the device, is accompanied by mechanical agitation of the powder receptacle. Such agitation facilitates the release of powder from the powder receptacle, and may also give a more uniform distribution of powder material dispensed from the device.

The powder receptacle may be an integral part of the device according to the invention, such that the device is supplied with a quantity of powder contained within the powder receptacle. In such a case, the device may be a disposable device, which is discarded after the desired quantity of powder has been dispensed from the powder receptacle.

Alternatively, the powder receptacle may be a separate component that is coupled to the device prior to use. In such a case, the powder receptacle, containing a quantity of powder, is typically supplied with a closure that is removed to enable the receptacle to be coupled to the device. The device and the receptacle may be formed with cooperating formations that enable them to be coupled together. For example, the device may be formed with an upstand or spigot that is received within or about a neck of the powder receptacle.

In currently preferred embodiments, the powder receptacle is supplied in the form of a sealed vial, e.g., of glass, that contains a quantity of powder. The vial has a neck that is sealed by a removable closure. When the closure is removed, a device according to the invention is engaged with the vial, by insertion into the neck of the vial of a tubular spigot that has an interference fit with the interior of the neck. When the vial, which is coupled to the device, is then inverted, powder in the vial falls into the spigot. In such an arrangement, loss of powder from the spigot is preferably inhibited or prevented by a perforated base member that extends across the interior of the spigot. Other embodiments of powder receptacle that may be used include cartridges, e.g., of plastics materials. Such receptacles may be supplied with closures that are removed prior to attachment of the cartridge to the device, or the device and the powder receptacle may be configured such that engagement of the powder receptacle with the device brings about opening of the powder receptacle. For instance, the powder receptacle may comprise a foil closure that is ruptured by appropriate formations on the device when the receptacle is engaged with the device.

The perforated base member retains the bulk of the powder within the powder receptacle prior to actuation of the gasflow generator, but permits powder to pass through the base member when the powder is entrained in the gasflow generated by actuation of the gasflow generator. The nature of the base member should therefore be such that the perforations in the base member are small enough that, when the powder rests upon the base member, its packing characteristics and angle of repose are such that the powder does not pass to any significant extent through the base member. On the other hand, the perforations should be such that, when the powder resting upon the base member is energized and entrained in the gasflow, it is able to pass through the perforations in the base member and be dispensed.

Conveniently, the base member takes the form of a perforated plate, which will typically be circular. Preferably, a substantial proportion, or the full extent, of the plate is perforated. The perforations in the base member may have any suitable shape, eg circular, square or hexagonal, and will typically be arranged in a regular array and/or uniformly across a substantial proportion, or even the full extent, of the base member.

Thus, according to another aspect of the invention, there is provided a device for the dispensing of a powder, the device comprising, or being adapted to be coupled to, a powder receptacle, the device further comprising, or being adapted to be coupled to, a gasflow generator adapted upon actuation to cause gas to flow into the powder receptacle, wherein the powder receptacle is oriented, in use, such that, prior to actuation of the gasflow generator, powder contained within the receptacle settles under gravity and is retained within the powder receptacle by, and rests upon, a perforated base member.

In such embodiments, the gasflow may enter the powder receptacle through the base member, thereby energizing powder resting upon the base member and causing said powder to be entrained in the gasflow and to pass through the base member into an outlet conduit, thereby to dispense said powder from the device. Gas is caused to flow through the perforated base member and this gasflow energizes the particles of powder resting upon the base member, in the sense of imparting kinetic energy to those particles and entraining them in the gasflow. In other embodiments, a channel or conduit is provided to conduct the gasflow to a point within the powder receptacle that is spaced from the perforated base member, so that the gasflow emerges into the powder bulk at a point that is above the powder particles resting on the base member. The energized particles are able to pass through the base member into an outlet conduit from which the powder particles entrained in the gasflow are dispensed.

In other embodiments, the gasflow is not directed at and through the perforated base member, but is caused to enter the outlet conduit in such a manner that powder is drawn from the powder receptacle and entrained in the gasflow. For instance, the gasflow may be directed into the outlet conduit through an appropriately shaped inlet, e.g., a slot, so that a jet of gas passes into the outlet conduit beneath the powder receptacle. The jet of gas may have a form that is dictated by the shape of the inlet and which is conducive to entrainment of powder material from the powder receptacle. For instance, the inlet may have the form of a slot that is disposed orthogonally to the plane of the perforated base member (i.e., in most configurations of the device, a vertical slot). In other embodiments, the inlet may have the form of a slot that is parallel to the plane of the perforated base member (i.e. usually a horizontal slot). Such a horizontal slot may conveniently be created as a clearance between components of the device that together define the outlet conduit (or at least that part of the outlet conduit that lies beneath the powder receptacle). In all such cases, a shaped jet of air is directed into the outlet conduit, beneath the powder receptacle. The relatively high velocity of that jet creates a venturi-type effect that draws air into it from the surroundings, thereby energizing powder at the base of the powder receptacle, drawing that powder from the powder receptacle, and entraining it in the gasflow.

Apart from retaining the powder material within the powder receptacle until energized by the gasflow, the perforated base member functions as a sieve, preventing large agglomerated particles passing through, and enhancing the uniformity of the powder material dispensed from the device. The high energy of the gasflow through the outlet conduit may also assist in deagglomerisation of the powder as it is dispensed from the device.

The gasflow generator may be either an integral part of the device according to the invention, or an external component to which the device is coupled. Where the gasflow generator is part of the device, it may take various forms. For instance, the gasflow generator may comprise a compressible bulb or bellows that can be manually compressed by the user. In such a case, the bulb or bellows is preferably resilient and may include a one-way valve or an opening that permits the ingress of air to permit the bulb or bellows to return to its expanded condition after pressure applied to it is released. In such embodiments, the gas is generally ambient air.

In other embodiments, the gasflow generator is a canister of a compressed gas or a liquefied propellant. Compressed gases include compressed air, and compressed hydrocarbons. Liquefied propellants include chlorofluorocarbons and hydrofluoroalkanes. In all such embodiments, the canister will generally be provided with a valve by which the gasflow can be controlled.

In yet further embodiments, the gasflow generator does not itself form part of the device according to the invention, but is an external gas source to which the device is coupled. In such embodiments the device may, for instance, be coupled to a compressed gas source by an appropriate conduit, e.g., a flexible tube. The gas line may be a compressed air line, though other compressed gases may be used, e.g., nitrogen or carbon dioxide. Again, the arrangement will generally include means by which the gasflow can be controlled. Typically, the device will include an actuator, e.g., of the push button type, by which the flow of gas can be controlled.

In the device according to the invention, actuation of the gasflow generator is effectively synchronized with actuation of the agitator. The arrangement may be such that actuation of the gasflow generator causes actuation of the agitator, or vice versa.

In certain embodiments of the invention, the agitator may be operably linked to the actuator by which the gasflow is controlled. For instance, the actuator may be coupled to a trigger mechanism that causes a striking element to impact upon the powder receptacle.

In other embodiments, the agitator may be driven by the gasflow, such that the agitator operates for as long as the gas flows and is disengaged when the flow of gas is halted. In presently preferred embodiments, the agitator includes a moveable element that is positioned within the gasflow path. Such a moveable element is preferably mounted such that its movement generates mechanical disturbances or vibrations within the device, leading to physical agitation of the powder contained within the powder receptacle. In particularly preferred embodiments, the path along which gas is caused to flow includes a loop within which an agitator element is driven. Conveniently, such a loop has the form of a circular track and the agitator element is a ball or the like that is driven around the track by the gas flow. The movement of the ball generates vibratory forces that are transmitted through the device to the powder receptacle. In other embodiments, agitation of the powder receptacle may be brought about by actuation of an electric motor or the like.

Powder is preferably discharged from the device according to the invention via a discharge tube or barrel. Such a discharge tube or barrel may be capable of a limited degree of orientational movement relative to the rest of the device, in order that the direction of flow of the discharged powder may be adjusted to suit the needs of the situation in which the device is used, e.g., to facilitate optimal delivery of the powder during a surgical procedure.

The device according to the invention will most commonly comprise components manufactured wholly or largely of plastics materials. Where appropriate, however, other materials such as metals, e.g., stainless steel, and glass, e.g., for the powder receptacle, may be employed. For medical applications, the materials used may be of suitable medical grade and sterilizable. For ease of use, the components of the device according to the invention may be incorporated into an outer housing that facilitates operation of the device. For instance, the device may be configured such that it can be readily held and operated in one hand.

The device according to the invention may be used to deliver a wide variety of powders to a surface of the body. Such powders include agents intended to have a therapeutic effect, either in terms of a pharmacological effect on the body or as disinfectants or the like useful in the prevention or treatment of infections. One particular field in which the device of the invention is useful, however, is for the delivery of haemostatic powder compositions to internal tissues exposed during surgical procedures or after traumatic injury. Such haemostatic compositions, which may also be described as tissue sealants, may for instance comprise dry powder mixtures of fibrinogen and thrombin. Such a mixture is essentially inert when formulated in the dry state, but once hydrated, e.g., upon application to a bleeding wound, the mixture leads to the production of fibrin which cross-links to form a blood clot.

Thus, according to a further aspect of the invention, there is provided a method of delivering a haemostatic composition to an internal tissue exposed during surgical procedures or after traumatic injury, which method comprises providing a device as described above, which device is charged with a quantity of a haemostatic composition in dry powder form, and dispensing said composition from said device onto said tissue.

DESCRIPTIONS OF THE DRAWINGS

Embodiments of the invention will now be described in greater detail, by way of illustration only, with reference to the accompanying drawings, in which.

DETAILED DESCRIPTION OF THE EMBODIMENTS

Figure 1:
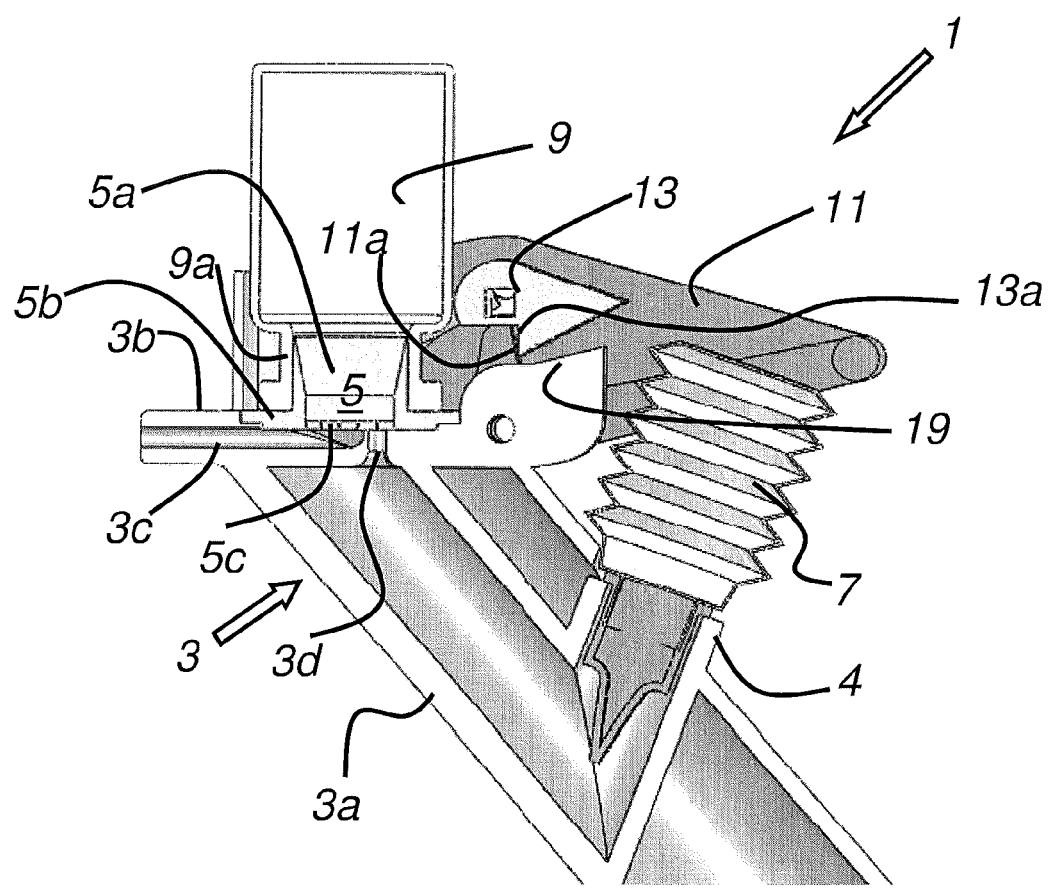
FIG. 1 is a schematic side view of a first embodiment of a powder delivery device according to the invention, partly in section, and showing a trigger mechanism in a rest condition.

Referring first to FIG. 1, a first embodiment of a powder delivery device according to the invention is generally designated 1 and comprises a main body 3 to which is fitted an upstanding tubular spigot 5 and a bellows 7. A glass vial 9 containing a quantity of the powder to be dispensed is engaged with the spigot 5, as described below.

The main body 3 is injection molded in plastics material with the general shape of a pistol. A downwardly (as viewed in FIG. 1) depending hollow limb 3a of the main body 3 is adapted to be held by a user, and has a socket 4 with which the bellows 7 is engaged. A horizontal (as viewed in FIG. 1) limb of the main body 3 has an internal bore 3c and constitutes a barrel 3b along which powder is dispensed from the device 1.

The spigot 5 is also molded in plastics material. The spigot 5 comprises an upwardly (as viewed) directed tubular connector 5a with a peripheral flange 5b at its lower extremity. The flange 5b is received within a correspondingly shaped recess in the upper surface of the main body 3, the flange 5b and main body 3 being bonded together.

The internal bore of the spigot 5 is tapered such that it has a funnel-like form, the base of the bore being closed by a perforated plate 5c that is formed integrally with the rest of the spigot 5. The bore 3c within the barrel 3b terminates beneath the perforated plate 5c. The end of the bore 3c that lies beneath the plate 5c is upwardly open so as to be in communication with the perforations in the plate 5c and hence with the internal bore of the spigot 5 and the vial 9. The bellows 7 comprises a concertina-type chamber, one end of which is fitted with a nozzle. The bellows 7 is formed in plastics material and has a certain degree of resilience, such that it can be manually compressed, but returns to the expanded configuration shown in FIG. 1 when the pressure applied to it is released. The other end of the bellows 7 may be provided with a one-way valve, e.g., a flap valve (not visible in FIG. 1) to permit the bellows 7 to fill with air when it expands back to the condition shown in FIG. 1. Alternatively, the end of the bellows 7 may simply be provided with an opening that is occluded, e.g., by the user's thumb, when the bellows is compressed and then exposed to permit the bellows 7 to expand back to the condition shown in FIG. 1.

The nozzle of the bellows 7 has an interference fit within the socket 4. A conduit 3d connects the interior of the downwardly depending limb 3a and the spigot 5. In particular, the conduit 3d provides for the passage of air expelled from the bellows 7 through a region of the perforated plate 5c adjacent to that part which overlies the end of the bore 3c.

The vial 9 has a neck 9a that receives the tubular connector 5a with an interference fit. The vial 9 is supplied with a closure that seals the neck 9a. With the vial 9 in an upright position, the closure is removed and the tubular connector 5a inserted into the neck 9a. The assembly is then an inverted condition, relative to the orientation shown in FIG. 1. The assembly is turned through 180°, to the condition shown in FIG. 1, whereupon powder contained within the vial 9 falls under gravity and fills the internal bore of the tubular connector 5a. The powder rests upon the perforated plate 5c, little or no powder falling through the perforations in the plate 5c.

Figure 2:
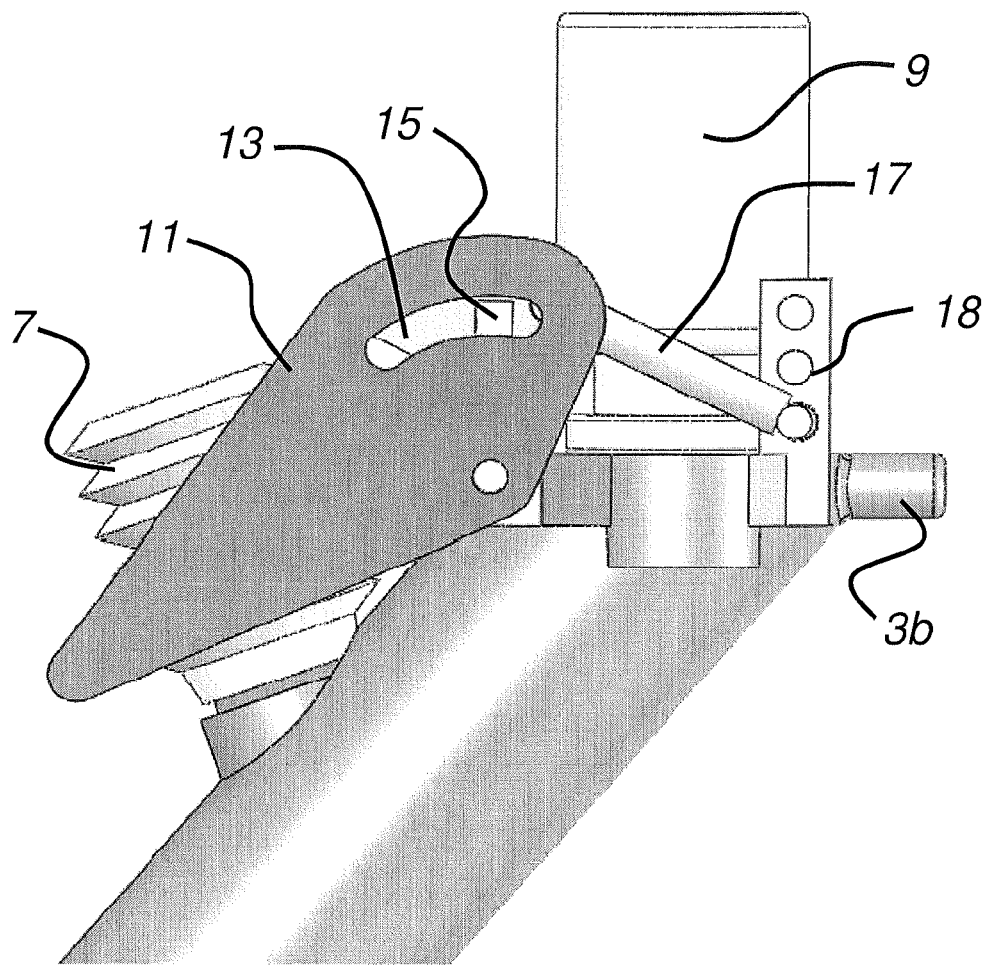
FIG. 2 is a view similar to FIG. 1, but from the other side of the device, and showing the trigger mechanism in an actuated condition.

A trigger 11 is pivotally mounted adjacent to the rear (i.e. the side distal to the barrel 3b) of the vial 9. The trigger 11 carries a striker 13 that is mounted to an arcuate track 15, such that the striker 13 is capable of a restricted range of movement relative to the trigger 11. A tension spring 17 (see FIG. 2) is mounted between the striker 13 and an upstand 18 on the main body 3, close to the front of the vial 9, so as to draw the striker 13 towards the vial 9.

As can be seen in FIG. 1, the trigger 11 and the striker 13 are formed with cooperating detents 11a, 13a, such that when the trigger 11 is pressed down by a user (as described below), the striker 13 is drawn away from the surface of the vial 9, against the action of the spring 17.

The rear part of the main body 3 is formed with a ramp 19. As the trigger 11 is depressed, the ramp 19 comes into contact with the striker 13. Continued depression of the trigger 11 causes the ramp 19 to displace the striker 13 and to disengage the detents 11a, 13a. When released from the trigger 11 by the ramp 19, the striker 13 is drawn by the action of the spring 17 into contact with the vial 9, thereby jarring the vial 9. In practical embodiments of the device 1, the trigger 11 is housed within a push button-type actuator (not shown), depression of which also results in compression of the bellows 7. Thus, generation of an airflow is synchronized with mechanical jarring of the vial 9, thereby facilitating entrainment of powder in the airflow and releasing powder from the vial 9.

To dispense powder from the device 1, the user holds the device 1 in a generally upright orientation, as shown in FIG. 1, and directs the barrel 3b at the intended site of application of the powder. The user then depresses the actuator, compressing the bellows 7 and depressing the trigger 11. Appropriate formations (not shown) may be provided on the device 1 to facilitate gripping of it, e.g., so that the actuator can be depressed by the thumb. Compression of the bellows 7 causes a jet of air to be directed through the conduit 3d. This jet of air passes through the perforated plate 5c and impacts upon the powder resting upon that plate 5c. Simultaneously, the striker 13 is drawn away from the vial 9, then released from the trigger 11 by the action of the ramp 19, with the result that the striker 13 impacts upon the vial 9 as the jet of air impacts upon the powder. The energized powder is entrained in the flow of air that escapes from the device 1 by passing back through the perforated plate 5c and along the internal bore 3c of the barrel 3b. The powder is blown out of the device 1 and deposited on the site of application.

When pressure is removed from the actuator, the bellows 7 relaxes to the condition shown in FIG. 1, air being drawn into the bellows through the one-way valve or opening in the free end of the bellows 7. At the same time, the trigger 11 returns to its rest condition, as shown in FIG. 1, in which the detents 11a, 13a re-engage. Actuation may then be repeated as often as required. Powder may continue to be dispensed until the desired amount of powder has been dispensed, or until the vial 9 is exhausted, all the powder contained within it having been dispensed. Where the vial 9 becomes exhausted, it may be appropriate for it to be removed from the spigot 5 and replaced with a fresh vial, ie for the device to be reused with a fresh vial of powder. In other circumstances, the device may be used only once and then discarded.

Turning now to FIGS. 3 to 7, a second embodiment of a powder delivery device in accordance with the invention is generally designated 20. This embodiment differs from the first embodiment 1 in that it is used in conjunction with an external source of compressed gas, and in that the mechanism by which the vial is agitated during dispensing of powder is different.

Figure 3:
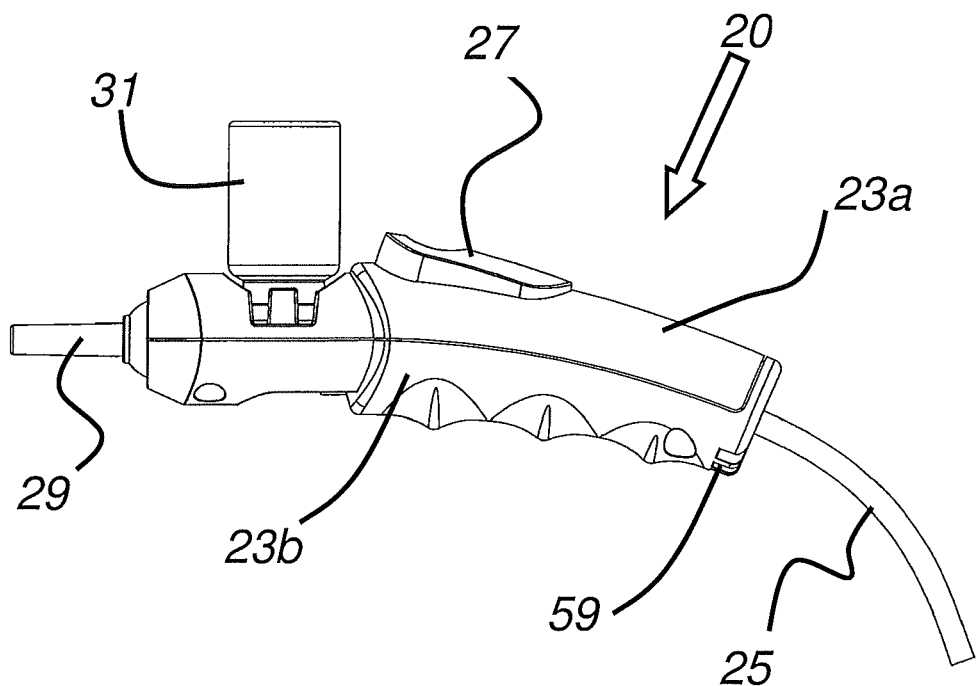
FIG. 3 is a side view of a second embodiment of a powder delivery device according to the invention.
Figure 4:
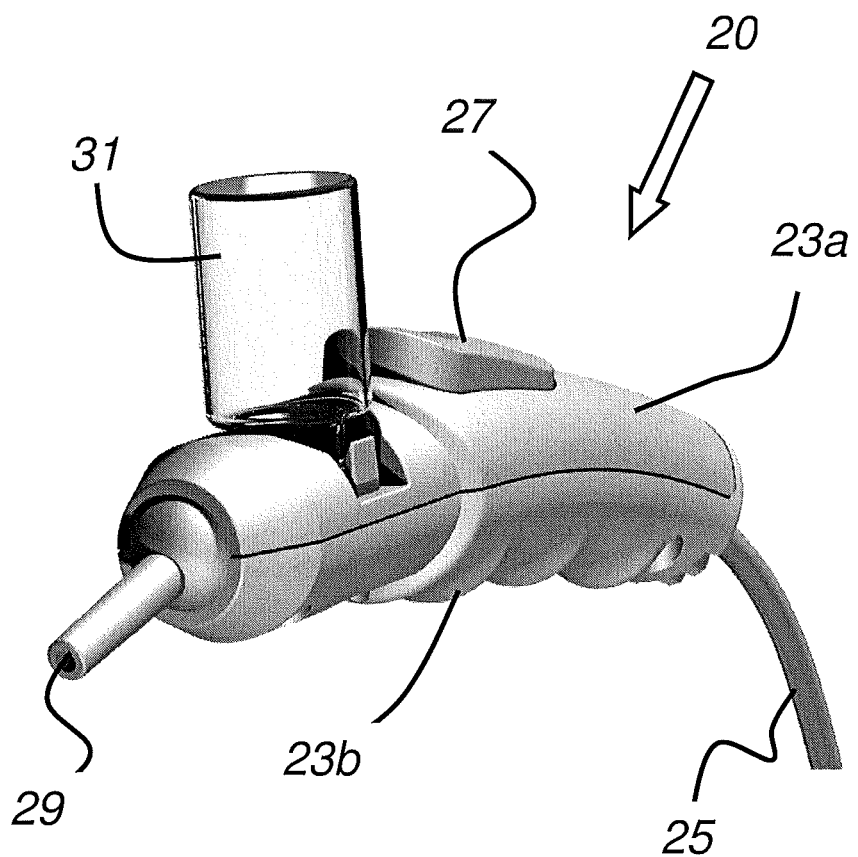
FIG. 4 is a perspective view of the device of FIG. 3.

Referring first to FIGS. 3 and 4, the device 20 has a main body that comprises upper and lower housing components 23a, 23b that are formed in plastics material by injection molding. The main body has the general form of an elongate cylinder that is adapted to be held a user's hand, the underside of the lower component 23b being shaped to facilitate such grip. A push button-type actuator 27 is mounted in the top of the main body such that, when the device 20 is held by the user, the actuator 27 can be depressed by the thumb of the hand that holds the device 20.

A flexible tube 25 extends from the rear end of the device 20 and is adapted to be connected to a gas source, e.g., a source of compressed air (not shown). A suitable connector (not shown) is provided at the distal end of the tube 25.

Figure 5:
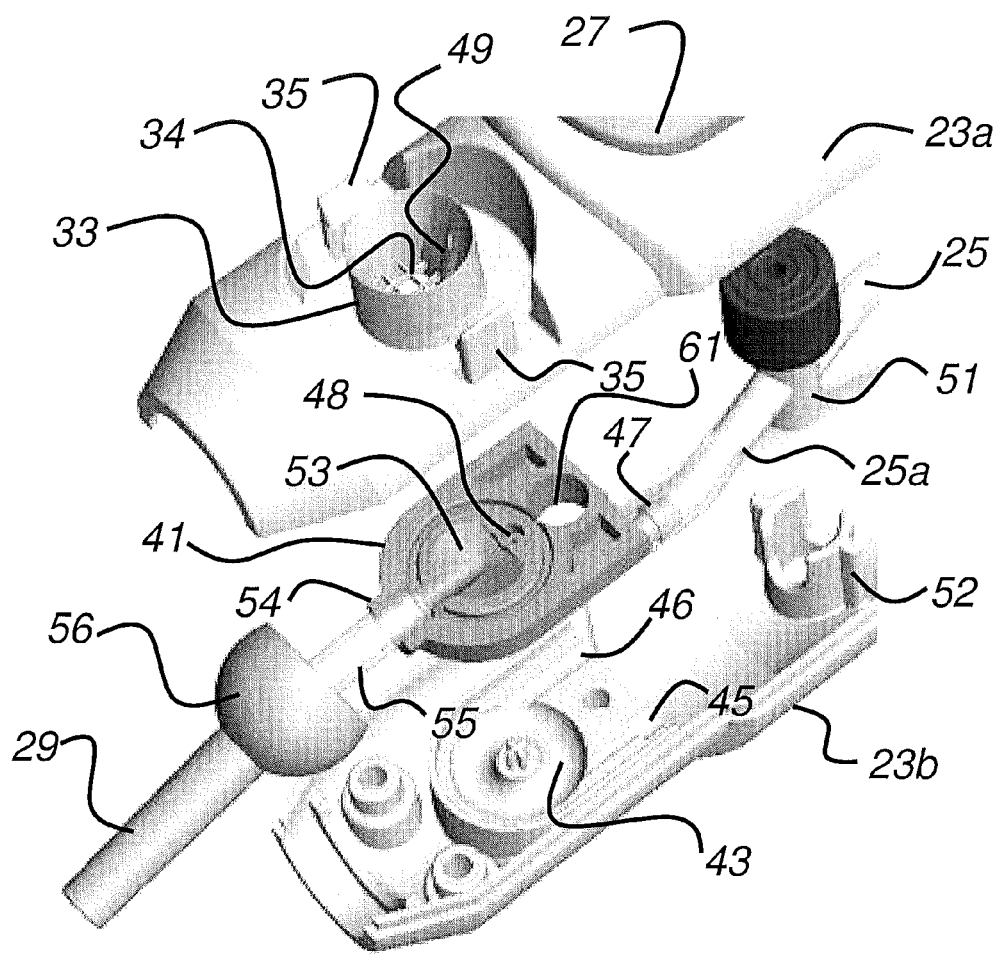
FIG. 5 is a partial exploded view of the device of FIG. 3.
Figure 6:
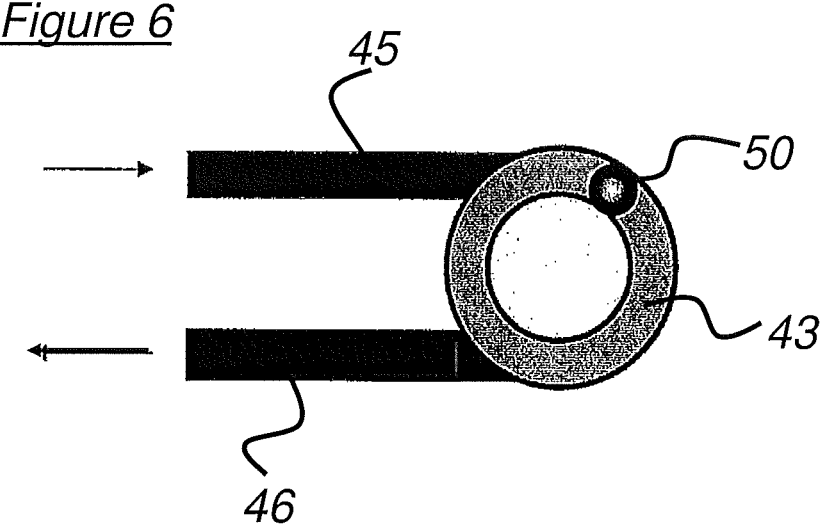
FIG. 6 is a schematic diagram illustrating the mechanism by which mechanical vibrations are generated during actuation of the device of FIG. 3.

The front end of the device 20 is provided with a tubular barrel 29, through which powder is dispensed from the device 20. A glass vial 31 is coupled to the device 20 in a similar manner to the way in which the vial 9 is coupled to the first embodiment of the device 1. As can be seen in FIG. 5, the upper component 23a is formed with an upstanding spigot 33 that is received within the mouth of the vial 31. A pair of clips 35 engages with a peripheral lip of the vial 31, so as to hold it securely in place. As in the first embodiment, the interior of the spigot 33 is tapered such that it has a funnel-like form, the base of the spigot 33 being closed by a perforated plate 34.

Referring again to FIG. 5, an intermediate component 41 is captivated between the upper and lower components 23a, 23b of the main body 23. The intermediate component 41 is formed with a circular opening 61 near its rear, which receives a downwardly depending boss (not visible in FIG. 5) formed integrally on the underside of the upper housing component 23a. A circular track 43 is formed in the lower component 23b, with air inlet 45 and outlet 46 channels. The intermediate component 41 cooperates with the lower component 23b to close the track 43. A ball 50 (not shown in FIG. 5) is held within the track 43 such that it can rotate freely around the circular track 43. The tube 25 is connected to a valve 51 that is held within an upstanding boss 52 formed integrally with the lower component 23b. The valve 51 is in turn connected to the intermediate component 41 by means of a short length of tubing 25a that is engaged with a tubular connector 47 formed integrally with that component and which, when the intermediate component 41 and lower component 23b are engaged, is in registration with the air inlet channel 45.

The valve 51 is positioned beneath the actuator 27, which is biased to the position shown in FIG. 3. The actuator 27 includes a cam (not visible in the drawings) which bears on the valve 51 to control the operation of the valve 51. When the actuator is depressed, the valve 51 is opened to permit air to flow from the external source of compressed air through the device 20, and when the actuator 27 is released the flow of air is halted.

Figure 7:
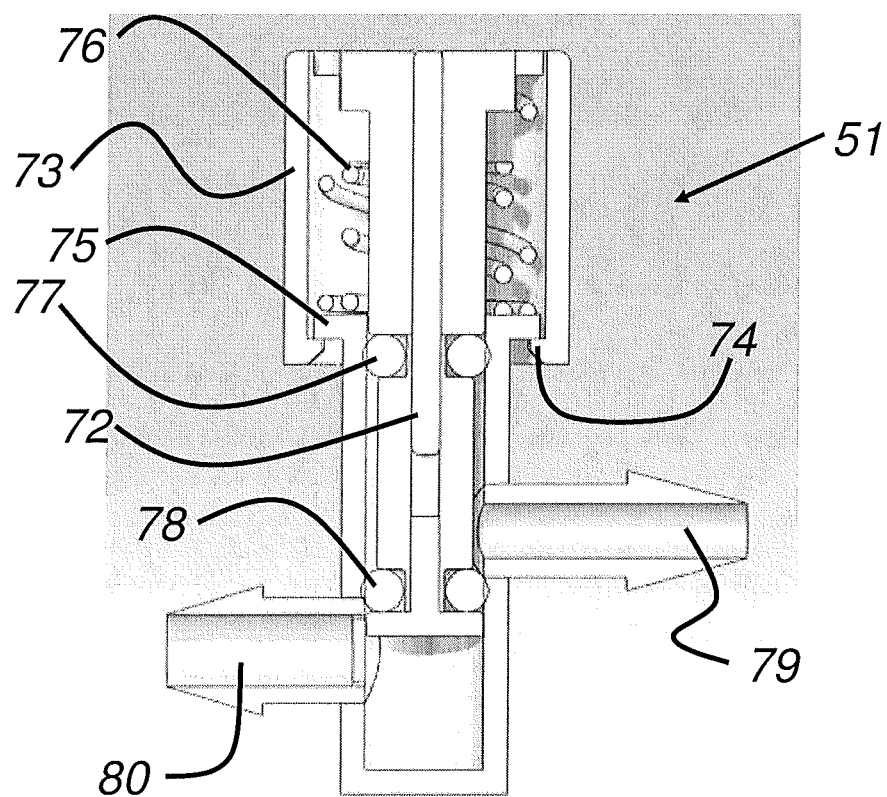
FIG. 7 is a cross-sectional view of a valve forming part of the device of FIG. 3.

The valve 51 is shown in cross-section in FIG. 7. It is of the type commonly referred to as a trumpet valve, and comprises a valve body 71 within which a valve stem 72 is capable of restricted reciprocating movement. The lower part of the valve stem 72 is of reduced dimensions, relative to the lower part of the valve body 71, so that an annular space exists between those two components. A valve cap 73 is mounted about the upper part of the valve stem 72. The range of movement of the valve stem 72 is restricted by engagement of an inwardly directed lip 74 at the base of the valve cap 73 with an outwardly directed flange 75 at the top of the valve stem body 71. The valve stem 72 is biased to the position shown in FIG. 7 by an arrangement of two compression springs 76 that act between the flange 75 and the underside of the top of the valve cap 73.

A pair of spaced apart O-rings 77,78 provide for sealing engagement between the valve stem 72 and the internal walls of the valve body 71. A valve inlet 79 receives the end of the tube 25, and a similar valve outlet 80 is connected to the short tube 25a that leads to the intermediate component 41.

In the position shown in FIG. 7, the valve 51 is closed. Passage of gas from the supply tube 25 to the valve outlet 80 is blocked. Depression of the valve stem 72, for example by the user pressing on the actuator 27, displaces the lower O-ring 78 to a position below the valve outlet 80, thereby opening the valve 51 and enabling flow of gas through the annular space surrounding the valve stem 72 to the valve outlet 80.

When the valve 51 is open, gas flows into the track 43 and drives the ball (not shown) around the track 43. An air feed hole 48 is formed in the intermediate component 41, above the rear portion of the track 43. This creates a flow of a certain amount of air from the track 43, that airflow being directed at the rear part of the perforated plate 34 and into a short feed pipe 49 that is formed integrally with the internal wall of the spigot 33 and terminates a short distance above the perforated plate 34, within the powder that, as in the first embodiment, rests upon the perforated plate 34. The feed hole 48 and feed pipe 49 direct a minor proportion of the airflow into the powder. The greater proportion of the airflow, however, is simply vented via the outlet channel 46. Openings 59 at the rear of the device permit vented air to escape. The proportion of the airflow that is directed into the vial 31 can be adjusted to suit the intended application of the device (ie to suit the amount of powder to be delivered, the nature of the powder, and so on) by varying the sizes of the feed hole 48 and/or the outlet channel 46.

The upper surface of the intermediate component 41 is formed, in the region beneath the perforated plate 34, with a shallow well 53 with a forwardly-directed outlet 54. The outlet 54 is connected, via a short tube 55, to the barrel 29. A nose 56 is formed integrally with the barrel 29 and is captivated between the forward ends of the upper and lower components 23a, 23b. The nose 56 is generally hemispherical in shape, and is held within the end of the housing in the manner of a ball-and-socket joint, which permits a restricted range of orientational movement of the barrel 29 (as is most readily apparent from FIG. 4).

To dispense powder from the device 20, the user holds the device 20 in one hand, directs the barrel 29 at the intended site of application of the powder, and depresses the actuator 27 with the thumb. This opens the valve 51, permitting air to flow through the device 20. Air flows along the tubes 25 and 25a into the track 43. The circulation of air within the track 43 causes the ball 50 to rotate rapidly around the track 43. The movement of the ball 50 causes a degree of mechanical vibration that is transmitted to the intermediate component 41, the upper component 23a and the vial 31.

Most of the airflow is vented from the device 20 via the outlet 46 and openings 59. However, a small proportion of air escapes from the track 43 via the feed hole 48, from which it is directed at the underside of the perforated plate 34 and into the feed pipe 49. This jet of air passes into the powder resting upon that plate 34. The mechanical agitation of the device 20 caused by rotation of the ball 50 within the track 43 facilitates the release of the powder from the vial 31. The powder is entrained in the flow of air that escapes from the device 20 by passing back through the perforated plate 34 into the well 53 and through the barrel 29. The powder is blown out of the device 1 and deposited on the site of application.

Mechanical agitation of the device continues for as long as the actuator 27 is depressed. When the actuator 27 is released, the flow of air is halted and the ball 50 ceases its rotary motion within the track 43. The device may be actuated for a continuous period, or intermittently.

As for the first embodiment 1, powder may continue to be dispensed until the desired amount of powder has been dispensed, or until the vial 31 is exhausted, all the powder contained within it having been dispensed. Where the vial 31 becomes exhausted, it may be removed from the spigot 33 and replaced with a fresh vial, or the device may be discarded, as appropriate.

Turning now to FIGS. 8 to 11, a third embodiment of a powder delivery device according to the invention is generally similar to that of FIGS. 3 to 7, but differs in the manner in which the gasflow entrains powder from the powder receptacle. Elements of the third embodiment that correspond to those of the second embodiment are identified by the same reference numbers, but with the prefix "1". Thus, the intermediate component 143 corresponds to the intermediate component 43 of the second embodiment, the perforated base member 134 corresponds to the base member 34, and so on.

Figure 8:
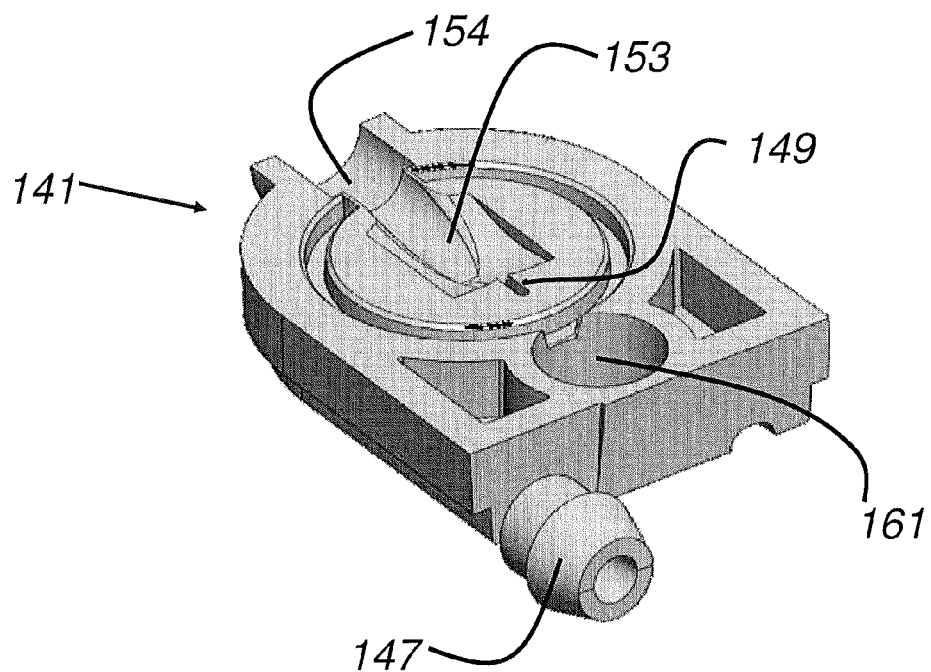
FIG. 8 is a perspective view of an alternative form of an intermediate component that forms part of a third powder delivery device according to the invention, that has a similar general form to that of FIG. 3.
Figure 9:
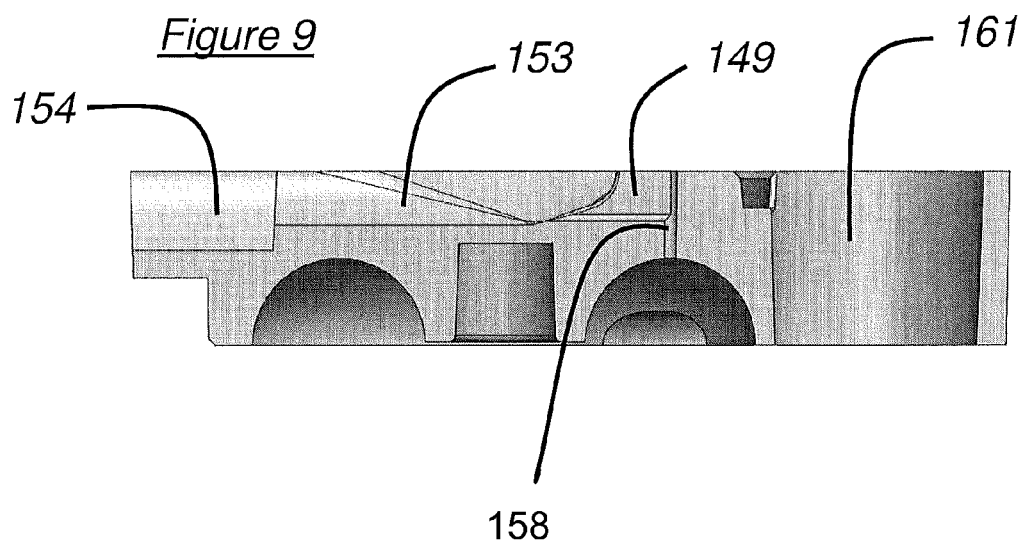
FIG. 9 is a cross-sectional view of the intermediate component of FIG. 8.
Figure 10:
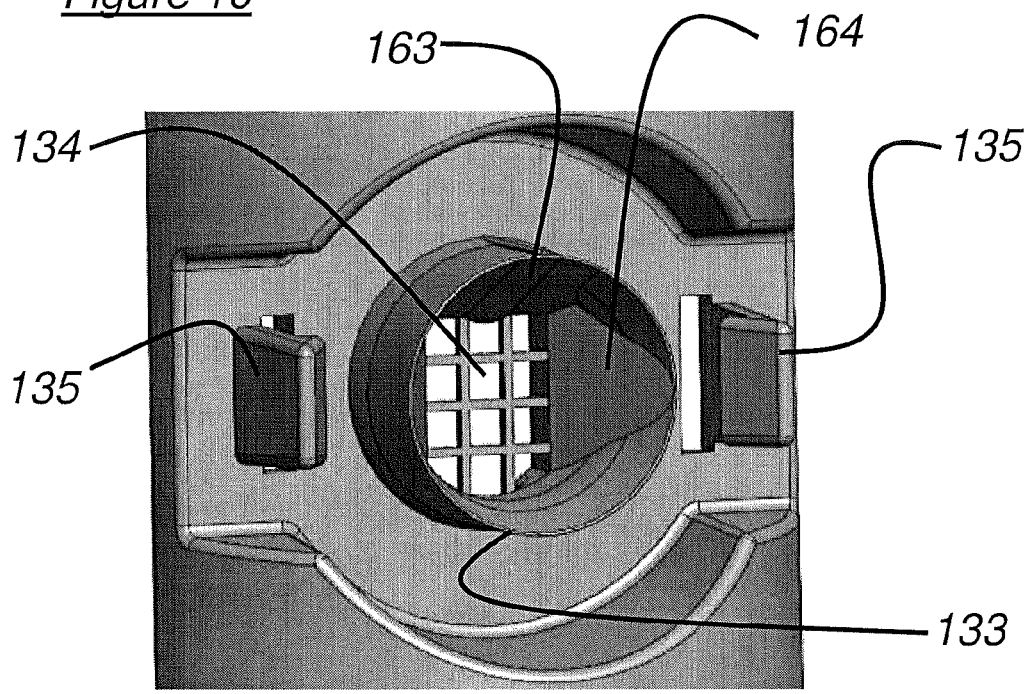
FIG. 10 is a fragmentary perspective view of an upper housing component employed in conjunction with the intermediate component of FIGS. 8 and 9.
Figure 11:
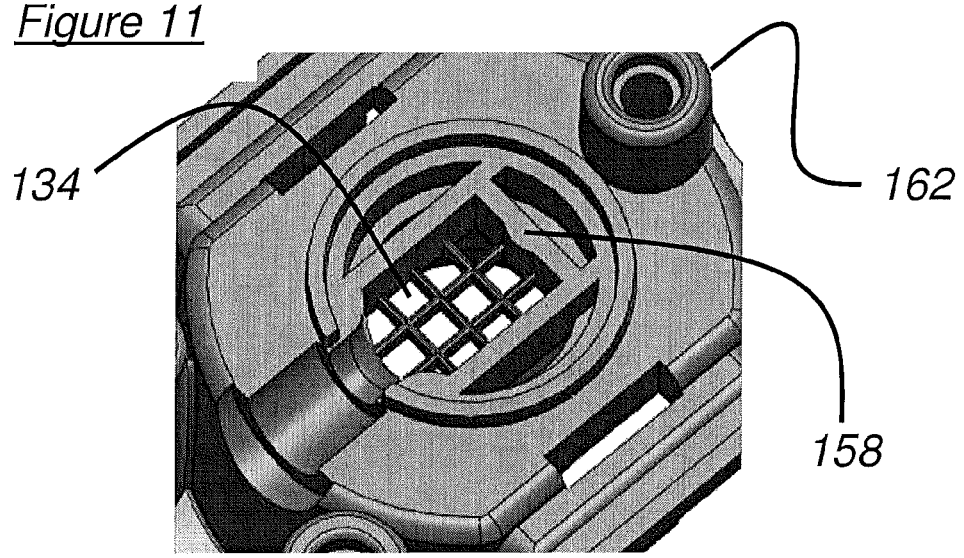
FIG. 11 is a fragmentary underside view of the upper housing component of FIG. 10.

FIGS. 8 and 9 show, in perspective and cross-sectional views respectively, an intermediate component 141 similar in general form to the intermediate component 41 of the embodiment of FIGS. 3 to 7. FIGS. 10 and 11 show fragmentary views of the part of the upper housing component 123a that contains the perforated base plate 134. In this embodiment, the lower housing component, barrel, valve and actuator (not shown) are identical to those of the second embodiment. The principal difference between the second and third embodiments lies in the manner in which air flows from the track 43 to the well 153 in the intermediate component 141 that is located beneath the perforated plate 134. In the second embodiment (FIG. 5), that air passes through feed hole 48 and feed pipe 49 to a position within the spigot 33 that is above the perforated plate 34. In the third embodiment, on the other hand, there is no feed pipe. Instead, feed hole 148 terminates in a vertical slot 149, the upper end of which is closed by an abutting part 158 of the undersurface of the upper housing component 123a (see FIG. 11).

As can be seen in FIG. 10, the upper surface of the upper housing component 123a is similar to that of the second embodiment, in that it is formed with an upstanding spigot 133, the base of which comprises the perforated plate 134. However, the rear part of the interior of the spigot 133, that in the second embodiment is occupied by the feed pipe 49, is in this embodiment a simple ramp 163. The interior side walls of the spigot 133 are also formed as ramps 164, giving the interior of the spigot 133 a funnel-like form. The ramps 164 may be omitted, so that the perforated base plate 134 is generally circular, in which case the parallel ribs evident in FIG. 11 may also be omitted. In fact, the presently most preferred embodiment of the device has such modifications.

As in the second embodiment, the intermediate component 141 is formed with a circular opening 161 that receives a corresponding downwardly-depending boss 162 formed on the underside of the upper housing component 123a (see FIG. 11).

The device of the third embodiment is actuated in precisely the same manner as the second embodiment, i.e. the user depresses the actuator, thereby opening the valve and causing gas to flow into the track and to drive the ball around that track. Movement of the ball creates vibrations that are transmitted to the vial containing the powder that is to be dispensed. Some of the gasflow escapes from the track via the feed hole 148 and slot 149. That gas is directed as a jet across the well 153 beneath the perforated plate 134, towards the outlet 154. The relatively high velocity jet of gas that traverses the well 153 creates a venturi-type effect that draws powder through the perforated plate 134 and entrains it in the gasflow.

Figure 12:
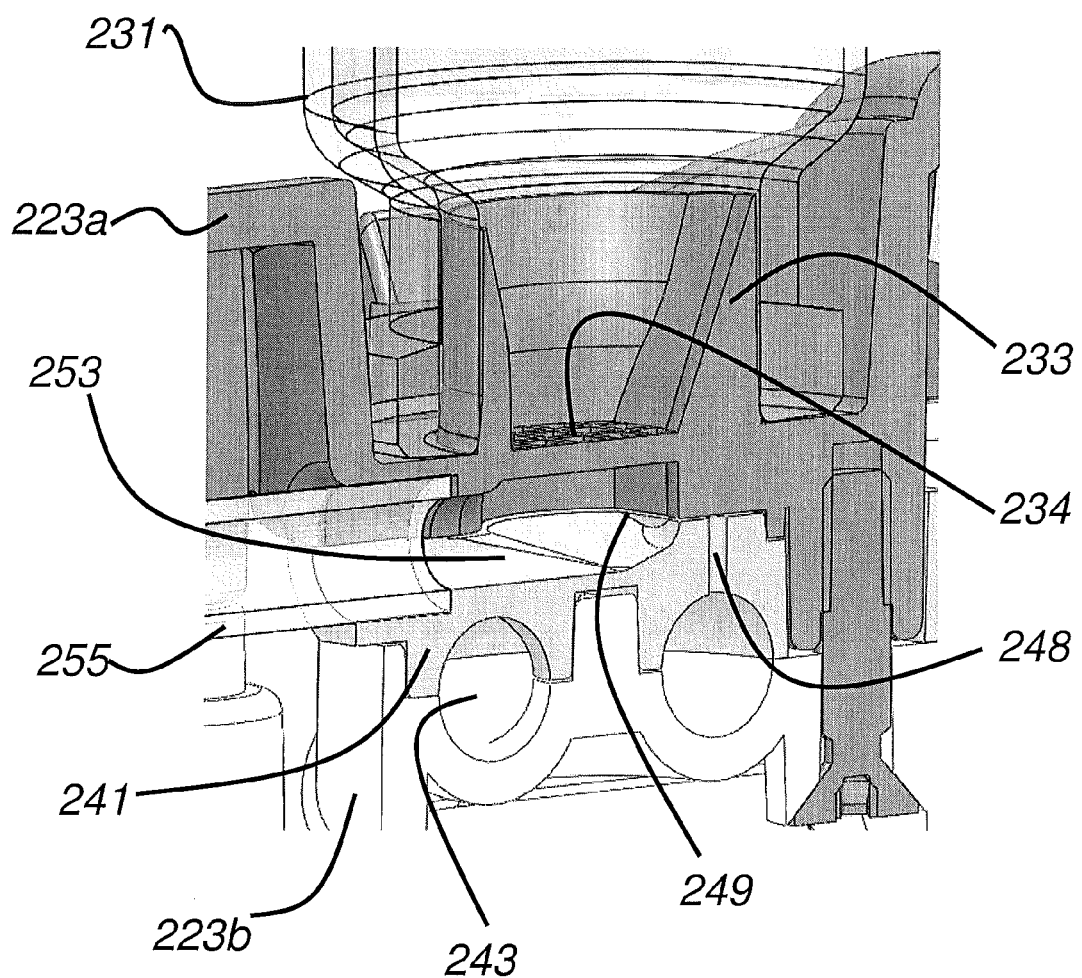
FIG. 12 is a fragmentary sectional view of a fourth embodiment of a powder delivery device according to the invention.

FIG. 12 shows a sectional view of a fourth embodiment of a powder delivery device according to the invention. Again, elements of this embodiment that correspond to those of the embodiment of FIGS. 3 to 7 are identified by corresponding reference numerals, but with the prefix "2". Thus, the intermediate component 243 corresponds to the intermediate component 43 of the second embodiment, the perforated base member 234 corresponds to the base member 34, and so on.

The fourth embodiment is again generally similar to the second and third embodiments just described. Thus, the fourth embodiment comprises upper and lower housing components 223a, 223b and an intermediate component 241. The upper housing component 223a is formed with an upstanding spigot 233 about which the neck of a vial 231 is received. The base of the spigot 233 is formed as a perforated plate 234. A well 253 is formed in the upper surface of the intermediate component 241 and is located beneath the perforated plate 234. Cooperating parts of the intermediate component 241 and upper housing component 223a together form an outlet 253 that is connected to a tube 255. The intermediate component 241 and lower housing component 223b together define a track 243 within which a ball (not shown) is driven, in use.

The fourth embodiment differs from the third in that the feed hole 248, that leads from the track 243, terminates not in a feed pipe (FIG. 5) or a vertical slot (FIG. 8), but in a planar horizontal gap 249 between the juxtaposed surfaces of the intermediate component 241 and the upper housing component 223a that surround the well 253.

The effect of the gap 249 is to create a high velocity jet of gas in a plane parallel to the perforated plate 243. As for the third embodiment, that jet of gas creates a venturi-type effect that draws powder through the perforated plate 243.

Figure 13:
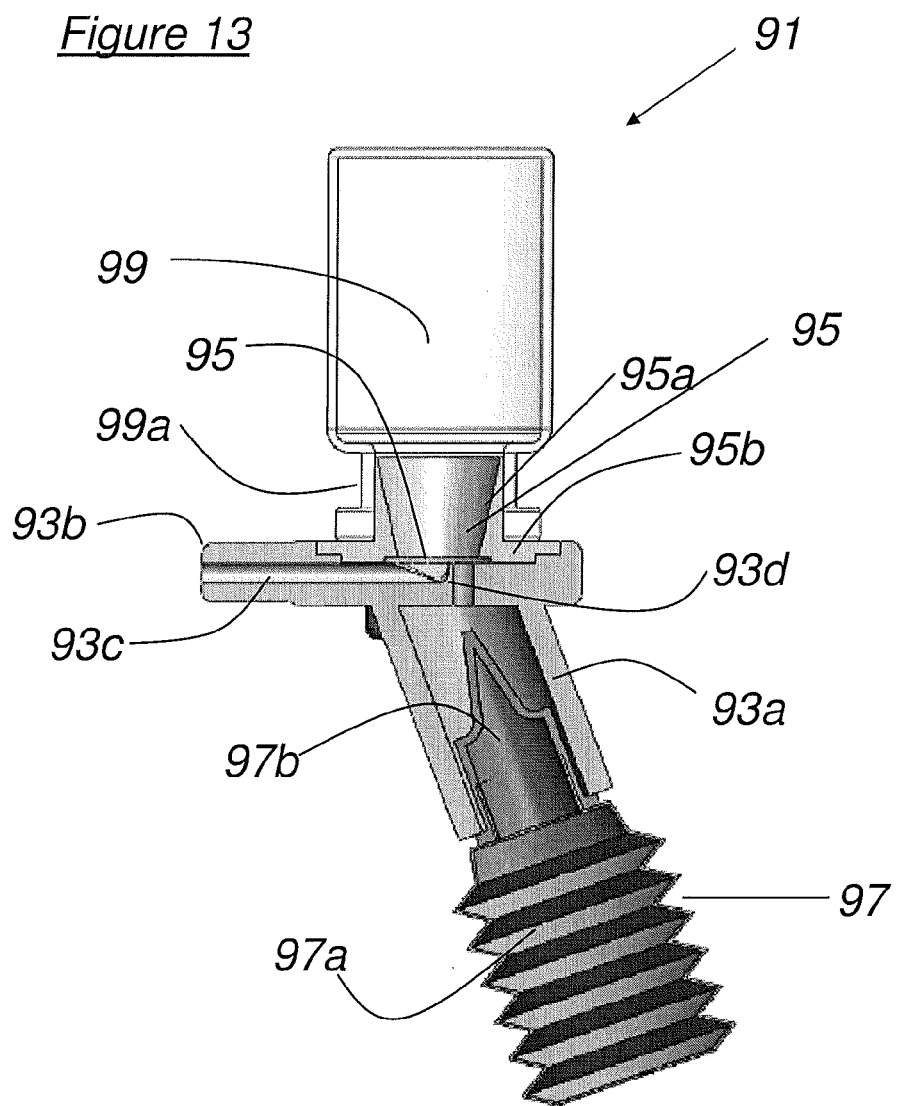
FIG. 13 is a sectional side view of a powder delivery device that is similar in concept to that of FIG. 1, save that generation of a gasflow is not accompanied by agitation of the powder receptacle according to the invention.
Figure 14:
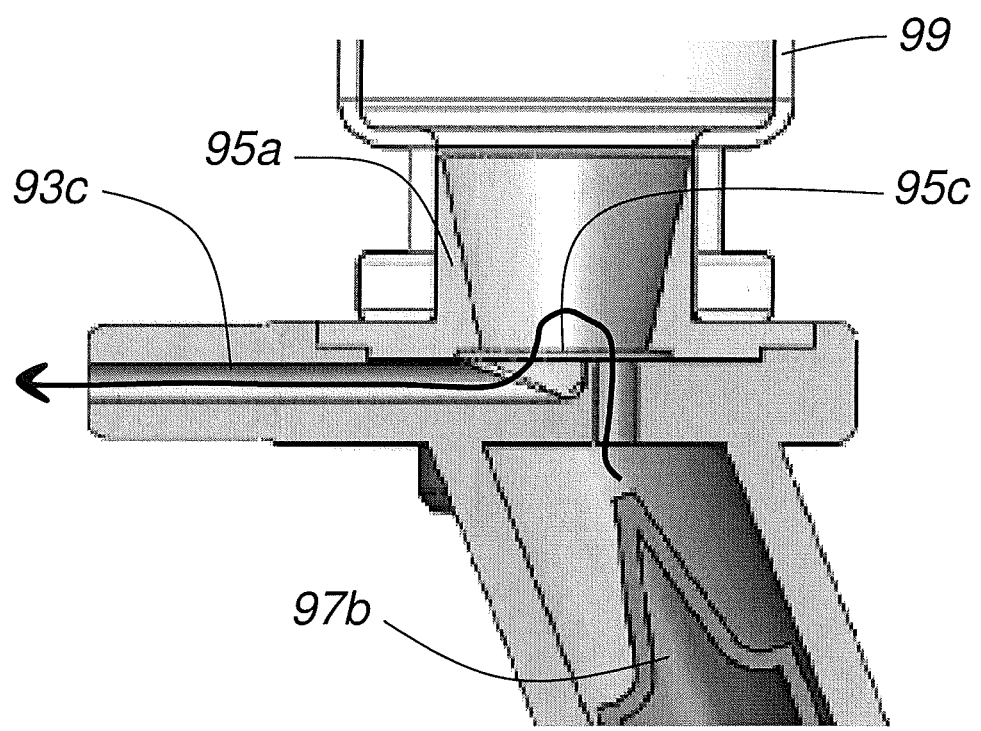
FIG. 14 is a fragmentary view, on an enlarged scale, of part of the device of FIG. 13, showing the flow of air into and out of a powder vial forming part of the device.

Referring finally to FIGS. 13 and 14, a further embodiment of a powder delivery device is generally designated 91 and comprises a main body 93 to which is fitted an upstanding tubular spigot 95 and a bellows 97. A glass vial 99 containing a quantity of the powder to be dispensed is engaged with the spigot 95, as described below.

The main body 93 is injection molded in plastics material and the general shape of a pistol. A downwardly (as viewed in FIG. 13) depending limb 93a of the main body 93 constitutes a tubular connector that receives the bellows 97. A horizontal (as viewed in FIG. 13) limb 93b of the main body 93 has an internal bore 93c and constitutes a barrel along which powder is dispensed from the device 91.

The spigot 95 is also molded in plastics material. The spigot 95 comprises an upwardly (as viewed) directed tubular connector 95a with a peripheral flange 5b at its lower extremity. The flange 95b is received within a correspondingly shaped recess in the upper surface of the main body 93, the flange 95b and main body 93 being bonded together.

The internal bore of the spigot 95 is tapered such that it has a funnel-like form, the base of the bore being closed by a perforated plate 95c that is formed integrally with the rest of the spigot 95. The bore 93c within the horizontal limb 93b of the main body 93 terminates beneath the perforated plate 95c. The end of the bore 93c that lies beneath the plate 95c is upwardly open so as to be in communication with the perforations in the plate 95c and hence with the internal bore of the spigot 95 and the vial 99.

The bellows 97 comprises a concertina-type chamber 97a, one end of which is fitted with a nozzle 97b. The bellows 97 is formed in plastics material and has a certain degree of resilience, such that it can be manually compressed, but returns to the expanded configuration shown in FIG. 13 when the pressure applied to it is released. The other end of the bellows 97 may be may be provided with a one-way valve, e.g., a flap valve (not visible in FIG. 13) to permit the bellows 97 to fill with air when it expands back to the condition shown in FIG. 13. Alternatively, the end of the bellows 97 may simply be provided with an opening that is occluded, e.g., by the user's thumb, when the bellows is compressed and then exposed to permit the bellows 97 to expand back to the condition shown in FIG. 13.

The nozzle 97b has an interference fit within the downwardly depending limb 93a of the main body 93 such that the nozzle 97b is closely received within that limb 93a, with the tip of the nozzle 7b directed at a conduit 3d that connects the interior of the downwardly depending limb 93a and the spigot 95. In particular, the conduit 93d provides for the passage of air expelled from the bellows 97 through a region of the perforated plate 95c adjacent to that part which overlies the end of the bore 93c.

The vial 99 has a neck 99a that receives the tubular connector 95a. The vial 99 is supplied with a closure that seals the neck 99a. With the vial 99 in an upright position, the closure is removed and the tubular connector 95a inserted into the neck 99a. The assembly is then an inverted condition, relative to the orientation shown in FIG. 13. The assembly is turned through 180°, to the condition shown in FIG. 13, whereupon powder contained within the vial 99 falls under gravity and fills the internal bore of the tubular connector 95a. The powder rests upon the perforated plate 95c, little or no powder falling through the perforations in the plate 95c.

To dispense powder from the device 91, the user holds the device 91 in a generally upright orientation and directs the horizontal limb 93b of the main body 93 at the intended site of application of the powder. The user then compresses the bellows 97. Appropriate formations (not shown) may be provided on the device 91 to facilitate gripping of it, e.g., between the thumb and first two fingers of one hand, and compression of the bellows 97. Compression of the bellows 97 causes a jet of air to be directed at and through the conduit 93d. This jet of air passes through the perforated plate 95c and energizes the powder resting upon that plate 95c. The energized powder is entrained in the flow of air that escapes from the device 91 by passing back through the perforated plate 95c and along the internal bore 93c of the horizontal limb 93b. The powder is blown out of the device 91 and deposited on the site of application.

The perforated plate 95c serves to retain the powder until it is energized and dispensed by the flow of air through the plate 95c, and also facilitates deagglomeration and dispersion of the powder in the airflow.

FIG. 14 shows (by means of the arrow) the flow of air into the powder retained within the interior of the tubular connector 95a and the vial 99, and the flow of air and entrained powder out of the device 91.

When pressure is removed from the bellows 97, it relaxes to the condition shown in FIG. 13, air being drawn into the bellows through the one-way valve or opening in the free end of the bellows 97. Repeated compression of the bellows 97 causes repeated dispensing of powder from the device 91. Powder may continue to be dispensed until the desired amount of powder has been dispensed, or until the vial 99 is exhausted, all the powder contained within it having been dispensed. Where the vial 99 becomes exhausted, it may be appropriate for it to be removed from the spigot 95 and replaced with a fresh vial, i.e. for the device to be reused with a fresh vial of powder. In other circumstances, the device may be used only once and then discarded.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A device for the topical dispensing of a powder comprising:
   a powder receptacle storing the powder;
   a gasflow generator adapted, in use, to cause gas to flow through the device, the gasflow generator being external to the device and comprising a connector which is adapted to be coupled to the gasflow generator;
   an actuator;
   a trumpet valve; and
   an agitator configured to mechanically vibrate the powder receptacle to release powder from the powder receptacle,
   the gasflow generator, the actuator, the valve and the agitator being operably linked such that actuation of the actuator causes the valve to open, permitting gas to flow through the device, actuating the agitator to cause the receptacle to be mechanically vibrated to release the powder and to entrain the powder that has been released from the powder receptacle in the gas flow, thereby to dispense powder from the device, wherein the agitator is driven by the gasflow, such that the agitator operates for as long as the valve is open and the gas flows and is disengaged when the flow of gas is halted, and wherein the agitator includes a moveable agitator element that is positioned within a path of the gasflow,
   wherein the powder is a haemostatic composition and the device is configured to dispense powder through a gas flow outlet to internal tissues exposed during surgical procedures or after traumatic injury, the powder being dispensed from the powder receptacle until the actuator is selectively unactuated by a user.

2. A device as claimed in claim 1, wherein the moveable agitator element is mounted such that its movement generates mechanical disturbances or vibrations within the device without contacting the powder, leading to physical agitation of the powder contained within the powder receptacle.

3. A device as claimed in claim 1, wherein the path of the gas flow includes a loop within which the movable agitator element is caused to rotate.

4. A device as claimed in claim 3, wherein the loop is a circular track and the movable agitator element is a ball that is driven around the track by the gas flow.

5. A device as claimed in claim 1, wherein the powder receptacle is a vial integrally engaged with the device, such that the device is supplied with a quantity of powder contained within the vial.

6. A device as claimed in claim 1, wherein the powder receptacle is a separate component that is coupled to the device prior to use.

7. A device as claimed in claim 6, wherein the device and the receptacle are formed with cooperating formations that enable them to be coupled together.

8. A device as claimed in claim 7, wherein the device is formed with an upstand or spigot that is received within or about a neck of the powder receptacle.

9. A device as claimed in claim 6, wherein the powder receptacle is supplied in the form of a sealed vial that contains a bulk quantity of powder.

10. A device as claimed in claim 1, wherein the external gasflow generator is a source of compressed gas.

11. A device as claimed in claim 1, wherein the gasflow generator comprises a compressible bulb or bellows that can be manually compressed by the user.

12. A device as claimed in claim 1, wherein the gasflow generator is a canister of a compressed gas or a liquefied propellant.

13. A device as claimed in claim 1, which includes an outer housing that facilitates operation of the device.

14. A device as claimed in claim 13, wherein the outer housing is configured such that the device can be readily held and operated by the user in one hand.

15. A method of delivering the haemostatic composition to the internal tissue exposed during surgical procedures or after traumatic injury, which method comprises providing a device as claimed in claim 1, which device is charged with a quantity of the haemostatic composition in dry powder form, and dispensing said haemostatic composition from said device onto said exposed internal tissue.

16. A method as claimed in claim 15, wherein said haemostatic composition comprises fibrinogen and thrombin.

17. A device as claimed in claim 1, wherein the gas flows along a first gas path configured to receive gas from a gas supply at one end of the first gas path and to exhaust the gas supply to atmosphere at another end of the first gas path, the gasflow in the first gas path driving the agitator, and wherein a portion of the gas in the first gas path is directed into a second gas path configured such that the gas in the second gas path entrains a quantity of powder from the powder receptacle.

18. A device for the topical dispensing of a powder comprising:
    a body;
    a powder receptacle storing the powder in fluid communication with the body;
    an agitator configured to vibrate the powder receptacle in response to a gas flow;
    a gas flow generator configured to generate the gas flow through:
       a first gas path entering the body configured to receive gas from a gas supply at one end of the first gas path to mechanically agitate the agitator and to exhaust the gas supply to atmosphere at another end of the first gas path; and
       a second gas path configured to direct a portion of the gas in the first gas path proximate the powder receptacle to entrain a quantity of powder released into the second gas path due to mechanical agitation by the agitator, the second gas path further configured to deliver the powder to a desired location;
    a valve; and
    an actuator, which is operably linked to the gasflow generator via the valve, and to the agitator, wherein the powder is dispensed to the desired location until the actuator is selectively unactuated by a user.

19. A device as claimed in claim 18, wherein the gas flow generator is an external gas flow generator, the device further comprising a connector which is adapted to be coupled to the external gas flow generator.

* * * * *